(12) United States Patent
Gunji

(10) Patent No.: US 9,459,143 B2
(45) Date of Patent: Oct. 4, 2016

(54) SPECTROSCOPIC DEVICE

(75) Inventor: Masahide Gunji, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 412 days.

(21) Appl. No.: 14/117,924

(22) PCT Filed: Jun. 21, 2012

(86) PCT No.: PCT/JP2012/065897
§ 371 (c)(1),
(2), (4) Date: Nov. 15, 2013

(87) PCT Pub. No.: WO2012/176851
PCT Pub. Date: Dec. 27, 2012

(65) Prior Publication Data
US 2014/0092383 A1    Apr. 3, 2014

(30) Foreign Application Priority Data

Jun. 24, 2011 (JP) .................................. 2011-140652

(51) Int. Cl.
*G01K 1/00* (2006.01)
*G01J 3/02* (2006.01)
(Continued)

(52) U.S. Cl.
CPC ................ *G01J 3/02* (2013.01); *G01J 3/0208* (2013.01); *G01J 3/0286* (2013.01); *G01J 3/0291* (2013.01);
(Continued)

(58) Field of Classification Search
CPC .................................................... G01J 3/0286
USPC .................................. 374/100; 356/72, 100
See application file for complete search history.

(56) References Cited

U.S. PATENT DOCUMENTS 5,739,905 A * 4/1998 Hutchinson ............... G01J 3/02
356/319
5,850,472 A * 12/1998 Alston ...................... G01J 3/10
382/162

(Continued)

FOREIGN PATENT DOCUMENTS

JP    2-101240 U    8/1990
JP    07-198597 A   8/1995

(Continued)

OTHER PUBLICATIONS

Office Action dated Feb. 24, 2015, issued in corresponding Japanese Patent Application No. 2013-521618, w/ English translation. (7 pages).

(Continued)

*Primary Examiner* — Lisa Caputo
*Assistant Examiner* — Nasir U Ahmed
(74) *Attorney, Agent, or Firm* — Westerman, Hattori, Daniels & Adrian, LLP

(57) ABSTRACT

A spectroscopic device includes a lamp house accommodating a light source inside, a spectrometer configured to disperse light from the lamp house, a temperature measurement means for measuring a temperature of the spectrometer, a heating means for heating the spectrometer, a storage means and a control unit. The storage means stores the detection temperature of the temperature measurement means at a time when an optical axis is stable in the spectrometer in a state where the light source is illuminated. The control unit is configured to control operation of the heating means, and to cause the heating means to operate, when the light source is illuminated from a light-off state, until a detection temperature of the temperature measurement means reaches the detection temperature stored in the storage means.

8 Claims, 5 Drawing Sheets

(51) Int. Cl.
*G01J 3/18* (2006.01)
*G01J 3/42* (2006.01)
*G01N 30/74* (2006.01)

(52) U.S. Cl.
CPC .. *G01J 3/18* (2013.01); *G01J 3/42* (2013.01); *G01N 30/74* (2013.01); *G01N 2201/0231* (2013.01); *G01N 2201/1211* (2013.01)

(56) References Cited

U.S. PATENT DOCUMENTS

| | | | |
|---|---|---|---|
| 8,013,293 B2 * | 9/2011 | Yamauchi | G01N 27/62 250/287 |
| 2005/0063186 A1 * | 3/2005 | Oda | F21V 29/02 362/294 |

FOREIGN PATENT DOCUMENTS

| | | |
|---|---|---|
| JP | 10-246670 A | 9/1998 |
| JP | 2000-74821 A | 3/2000 |
| JP | 2005-98765 A | 4/2005 |
| JP | 2005-257535 A | 9/2005 |
| JP | 2006-100416 A | 4/2006 |
| JP | 2007-064632 A | 3/2007 |
| JP | 2011-2310 A | 1/2011 |

OTHER PUBLICATIONS

International Search Report dated Oct. 9, 2012, issued in corresponding application No. PCT/JP2012/065897.

* cited by examiner

SPECTROSCOPIC DEVICE

TECHNICAL FIELD

The present invention relates to a spectroscopic device including a lamp house accommodating a light source inside, and a spectrometer for dispersing light from the lamp house.

BACKGROUND ART

FIG. 5 is a diagram schematically showing a configuration of a conventional spectroscopic device. Here, as an example of the spectroscopic device, a PDA (photodiode array) absorbance detector, for a liquid chromatograph, including a multiple wavelength detection function will be described.

As shown in FIG. 5, the spectroscopic device includes a lamp house 1, and a spectrometer 3.

A light source 5 is provided inside the lamp house 1. Light emitted from the light source 5 is radiated on the spectrometer 3 via an aperture plate (not shown).

The spectrometer 3 is provided with, in the order of passing of light, an aperture plate (not shown), a focusing mirror 7, a flow cell 9, a focusing mirror 11, a slit 13, a concave diffraction grating 15, and a photodiode array 17.

The lamp house 1 and the spectrometer 3 are arranged with a spacer 19 having an opening for light transmission therebetween.

Also, a fan 21 for cooling the lamp house 1 is provided to the spectroscopic device.

The lamp house 1 and the fan 21 are provided to suppress a change in the amount of light emission of the light source 5 due to a change in the ambient temperature of the device. Generally, the amount of light emission of the light source 5 changes according to a change in the temperature of the light source 5. When the amount of light of the light source 5 changes, the output value of the photodiode array 17 changes, and thus, high sensitivity measurement is possibly prevented. Accordingly, to prevent the output value of the photodiode array 17 from changing due to a change in the ambient temperature of the device, the light source 5 is accommodated in the lamp house 1 whose heat capacity is high to a certain degree and the lamp house 1 is cooled by the fan 21 with certain air volume so as to radiate heat, and the temperature of the light source 5 is thus not easily changed even if the ambient temperature of the device changes.

The spectroscopic device shown in FIG. 5 is a device for measuring an absorption spectrum of an analysis sample flowing into the flow cell 9, by emitting light radiated by the light source 5 on the flow cell 9 and causing the light which has passed through the flow cell 9 to be dispersed on the photodiode array 17 by the diffraction grating 15.

According to this spectroscopic device, when the light source 5 is illuminated from a light-off state, the spectrometer 3 is thermally expanded due to the heat generated by the light source 5, and the optical axis changes inside the spectrometer 3. Because of this influence, stabilization of the baseline of a chromatogram after the lighting of the light source 5 takes time.

PRIOR ART DOCUMENT

Patent Document

Patent Document 1: Japanese Patent Laid-open Publication No. 2000-74821

SUMMARY OF THE INVENTION

Problems to be Solved by the Invention

With conventional technology, increase in the temperature of the lamp house 1 is accelerated by temporarily stopping the fan 21 for cooling the lamp house immediately after the light source 5 has been illuminated, and increase in the temperature of the spectrometer 3 is accelerated through the increase in the temperature of the lamp house 1, to thereby reduce the stabilization time of the baseline of a chromatogram (for example, see Patent Document 1).

However, even if the time from the lighting of the light source until the temperature of the lamp house 1 is increased to a predetermined temperature is reduced, stabilization of the temperature distribution in the spectrometer 3 takes time, and it takes certain time for the optical axis to become stable in the spectrometer 3 and for the baseline of the chromatogram to become stable.

Such a problem is present not only with respect to the PDA absorbance detector for a liquid chromatograph, but also with respect to spectroscopic devices including a lamp house and a spectrometer, such as an absorption spectrophotometer, a spectrofluorometer, a UV detector for a liquid chromatograph, and a fluorescence detector. That is, a light source device including a lamp house and a spectrometer has a problem that it takes certain time for an optical axis to become stable in the spectrometer after the lighting of the light source.

The present invention has its object to reduce, for a spectroscopic device including a lamp house accommodating a light source inside, and a spectrometer for dispersing light from the lamp house, the time from the lighting of the light source until stabilization of an optical axis in the spectrometer.

Solutions to the Problems

A spectroscopic device according to the present invention is a spectroscopic device including a lamp house accommodating a light source inside, and a spectrometer configured to disperse light from the lamp house, and includes temperature measurement means for measuring a temperature of the spectrometer, heating means for heating the spectrometer, storage means for storing a detection temperature of the temperature measurement means at a time an optical axis is stable in the spectrometer in a state where the light source is illuminated, and a control unit configured to control an operation of the heating means, where the control unit causes the heating means to operate, when the light source is illuminated from a light-off state, until a detection temperature of the temperature measurement means reaches the detection temperature stored in the storage means.

With the spectroscopic device of the present invention, when the light source is illuminated from the light-off state, the spectrometer is heated by the heat from the lamp house, and it is also heated by the heating means until the detection temperature of the temperature measurement means reaches the detection temperature stored in the storage means.

The spectroscopic device of the present invention may further include a fan configured to cool the lamp house, where the control unit may keep the fan stopped when the light source is illuminated from the light-off state, and cause the fan to operate at a predetermined number of revolutions after the detection temperature of the temperature measurement means has reached the detection temperature stored in the storage means. Accordingly, increase in the temperature of the lamp house is accelerated compared to a case where the fan is operated from immediately after the lighting of the light source. Incidentally, with the spectroscopic device of the present invention, the fan may be operated at the predetermined number of revolutions or at a smaller number of revolutions than the predetermined number of revolutions until the detection temperature of the temperature measurement means reaches the detection temperature stored in the storage means.

Furthermore, the spectroscopic device of the present invention may include a plurality of sets of the temperature measurement means and the heating means for performing temperature measurement and heating of the spectrometer at different positions, where the storage means may store, for each temperature measurement means, the detection temperature of the temperature measurement means at a time the optical axis is stable in the spectrometer, and where the control unit may cause the plurality of heating means to operate based on the detection temperatures of the corresponding temperature measurement means. The temperature distribution of the spectrometer at a time the optical axis is stable in the spectrometer is thereby achieved faster compared to a case where there is one set of temperature measurement means and heating means, and the time from the lighting of the light source to the stabilization of the optical axis in the spectrometer is further reduced.

Furthermore, according to the spectroscopic device of the present invention, the storage means may store, instead of the detection temperature, a time after the light source is illuminated from the light-off state until the detection temperature of the temperature measurement means reaches the detection temperature at a time the optical axis is stable in the spectrometer according to an operation of the heating means, and the control unit may cause the heating means to operate, based on the time stored in the storage means. Also, in the case where the operation of the heating means is controlled based on the time stored in the storage means, as in the case where the operation of the heating means is controlled based on the detection temperature of the temperature measurement means, the spectrometer is appropriately heated, and the time from the start of lighting of the light source to stabilization of the optical axis in the spectrometer is reduced.

Effects of the Invention

A spectroscopic device of the present invention is a spectroscopic device including a lamp house accommodating a light source inside, and a spectrometer configured to disperse light from the lamp house, the spectroscopic device including temperature measurement means for measuring a temperature of the spectrometer, heating means for heating the spectrometer, storage means for storing a detection temperature of the temperature measurement means at a time an optical axis is stable in the spectrometer in a state where the light source is illuminated, and a control unit configured to control an operation of the heating means. Also, the control unit causes the heating means to operate, when the light source is illuminated from a light-off state, until a detection temperature of the temperature measurement means reaches the detection temperature stored in the storage means. Accordingly, when the light source is illuminated from the light-off state, the spectrometer is heated by the heat from the lamp house, and it is also heated by the heating means until the detection temperature of the temperature measurement means reaches the detection temperature stored in the storage means. Thus, compared to a case of no heating by the heating means, the temperature distribution of the spectrometer at a time the optical axis is stable in the spectrometer is achieved faster, and the time from the lighting of the light source to the stabilization of the optical axis in the spectrometer is reduced.

EMBODIMENTS OF THE INVENTION

Figure 1:
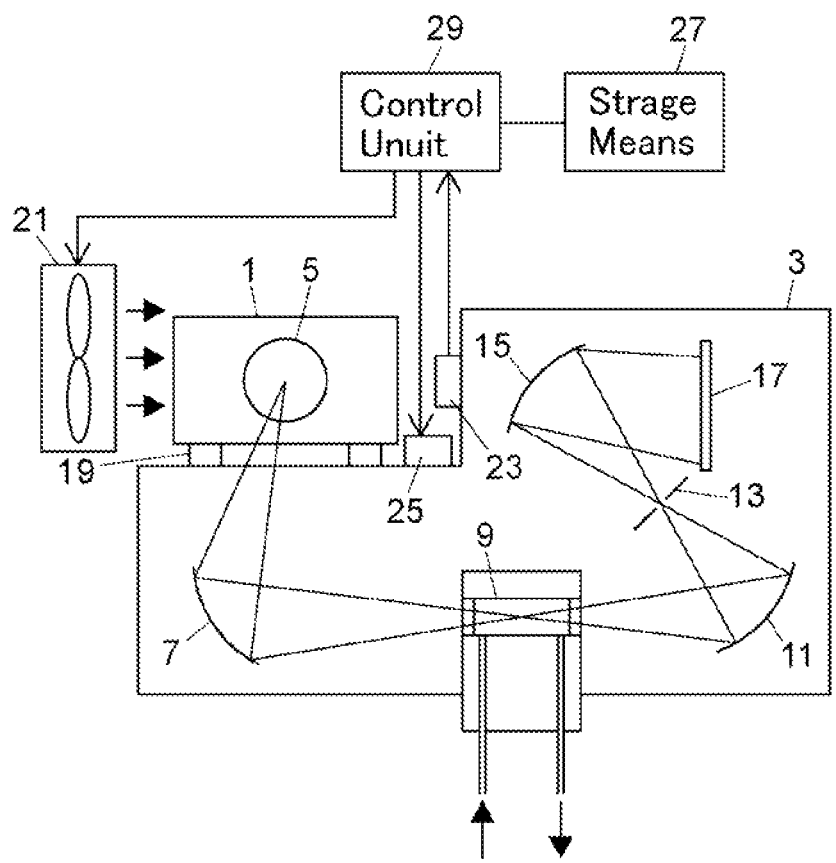
FIG. 1 is a diagram schematically showing a configuration of an embodiment.

FIG. 1 is a diagram schematically showing a configuration of an embodiment. Here, as an example of a spectroscopic device, a PDA absorbance detector, for a liquid chromatograph, including a multiple wavelength detection function will be described.

As shown in FIG. 1, the spectroscopic device includes a lamp house 1 and a spectrometer 3.

A light source 5 is provided inside the lamp house 1. A housing forming the lamp house 1 is formed of, for example, aluminum. As the light source 5, a discharge lamp such as a deuterium lamp, a tungsten lamp or the like is used. Light emitted from the light source 5 is radiated on the spectrometer 3 via an aperture plate (not shown) and a spacer 19.

The spectrometer 3 is provided with, in the order of passing of light, an aperture plate (not shown), a focusing mirror 7, a flow cell 9, a focusing mirror 11, a slit 13, a concave diffraction grating 15, and a photodiode array 17. A housing forming the spectrometer 3 is formed of, for example, aluminum. Light from the lamp house 1 is collected on the flow cell 9 by the focusing mirror 7. Light which has passed through the flow cell 9 is collected at the slit 13 by the focusing mirror 11. Light which has passed through the slit 13 is dispersed by the diffraction grating 15. The photodiode array 17 detects light intensity for light of a plurality of wavelengths from the diffraction grating 15.

The lamp house 1 and the spectrometer 3 are arranged with the spacer 19 having an opening for light transmission therebetween. The spacer 19 is formed of, for example, stainless steel.

Also, a fan 21 for cooling the lamp house 1 is provided to the spectroscopic device.

A thermistor 23 and a heater 25 are provided on an outer surface of the housing of the spectrometer 3. The thermistor 23 configures temperature measurement means for measuring the temperature of the spectrometer 3. The heater 25 configures heating means for heating the spectrometer 3.

Storage means 27 is provided for storing the detection temperature of the thermistor 23 at the time the optical axis in the spectrometer 3 is stable in a state where the light source 5 is illuminated.

A control unit 29 is provided for controlling the operation of the heater 25. The control unit 29 also controls the operation of the fan 21.

An operation of the embodiment will be described.

When the light source 5 is illuminated from a light-off state, the control unit 29 causes the heater 25 to operate, and heats the spectrometer 3. The control unit 29 causes the heater 25 to operate until the detection temperature of the thermistor 23 reaches the detection temperature stored in the storage means 27. The spectrometer 3 is thus heated by the heat from the lamp house 1, and also by the heater 25.

At this time, the control unit 29 keeps the fan 21 in a stopped state. Accordingly, increase in the temperature of the lamp house 1 is accelerated compared to a case where the lamp house 1 is cooled by the operation of the fan 21 immediately after the lighting of the light source 5.

When the detection temperature of the thermistor 23 reaches the detection temperature stored in the storage means 27, the control unit 29 stops the operation of the heater 25, and stops heating of the spectrometer 3 by the heater 25. Also, at the same time, the control unit 29 causes the fan 21 to operate at a predetermined number of revolutions to stabilize the temperature of the lamp house 1.

Figure 2:
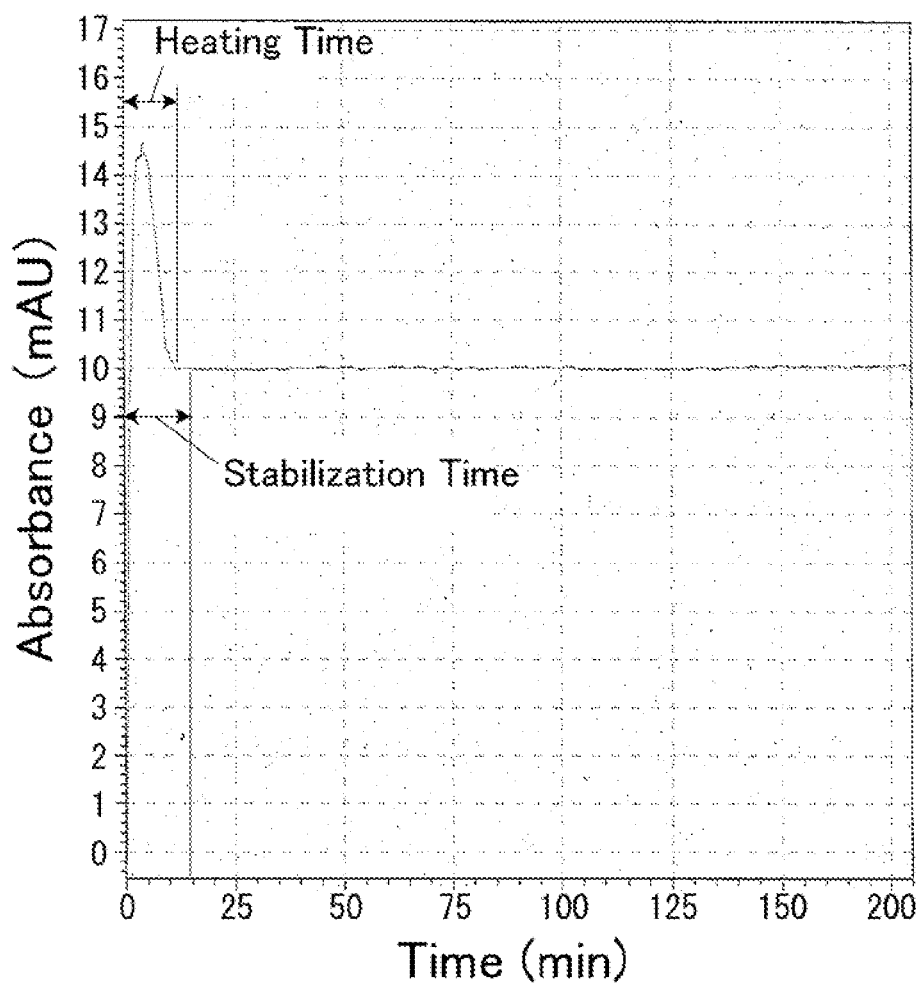
FIG. 2 is a diagram showing a change in a baseline of a chromatogram after lighting of a light source, according to the embodiment shown in FIG. 1.
Figure 3:
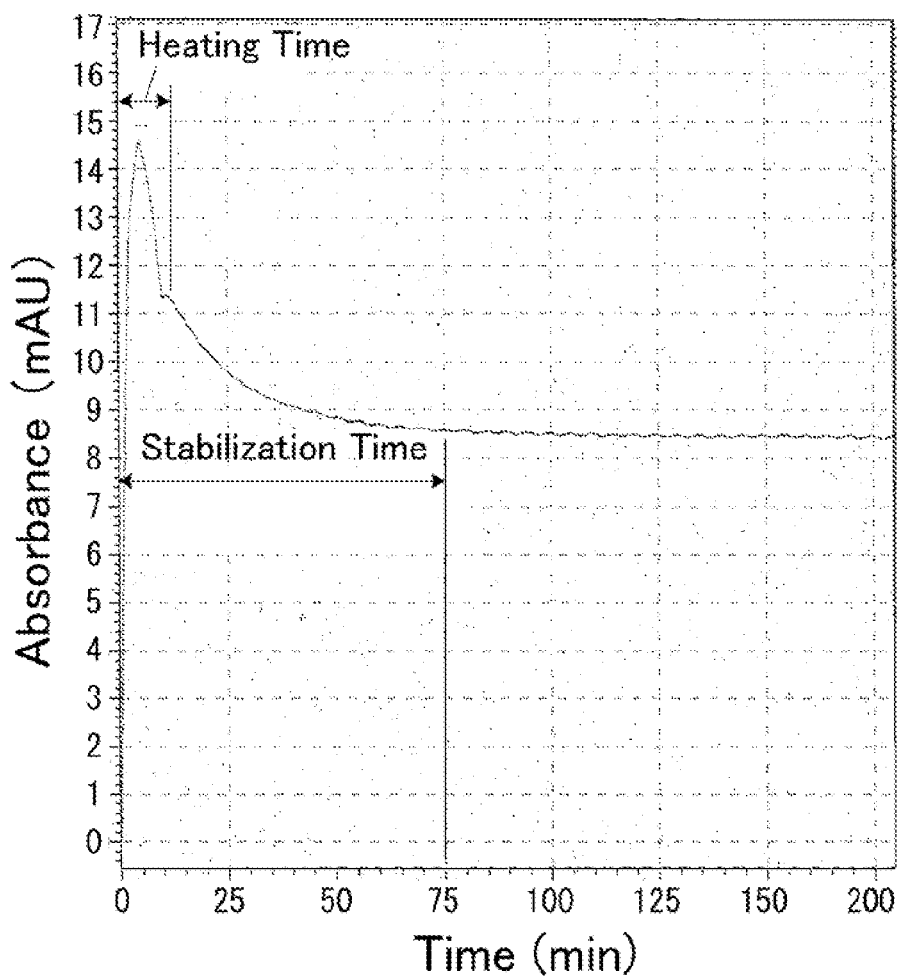
FIG. 3 is a diagram showing a change in a baseline of a chromatogram after lighting of a light source, according to a conventional technique.
Figure 5:
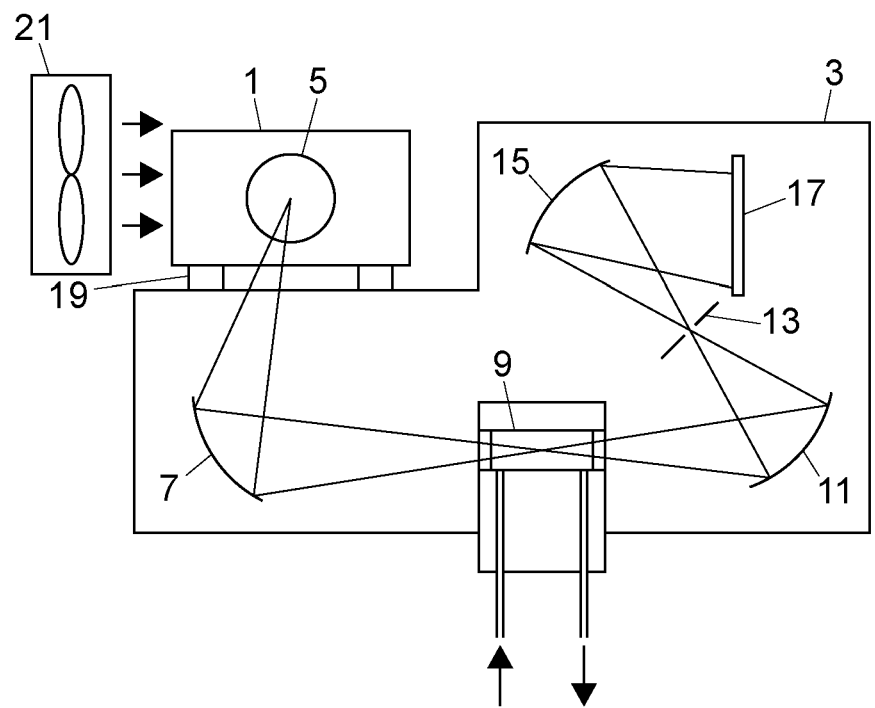
FIG. 5 is a diagram schematically showing a configuration of a conventional spectroscopic device.

FIG. 2 is a diagram showing a change in a baseline of a chromatogram after lighting of the light source, according to the embodiment shown in FIG. 1. FIG. 3 is a diagram showing a change in a baseline of a chromatogram after lighting of a light source, according to conventional technology shown in FIG. 5. In FIGS. 2 and 3, the vertical axes indicate the absorbance (arbitrary unit (mAU)), and the horizontal axes indicate time (minute). Absorbance at wavelengths of, for example, 250 nm (nanometer) and 4 nm is detected in the chromatograms in FIGS. 2 and 3. In the embodiment, the detection temperature of the thermistor 23 reaches the detection temperature stored in the storage means 27 in about 10 minutes (heating time) from the start of lighting of the light source 5. With conventional technology, the fan 21 is stopped for 10 minutes (heating time) from the start of lighting of the light source 5.

For example, it is assumed that the baseline is stabilized when the range of change of the baseline of the chromatogram is 0.5 mAU/h or less. As shown in FIG. 3, according to conventional technology, it takes about 75 minutes for the baseline to be stabilized from the start of lighting of the light source 5 (stabilization time). In contrast, as shown in FIG. 2, according to the embodiment, it takes about 15 minutes for the baseline to be stabilized from the start of lighting of the light source 5 (stabilization time). As described, the embodiment shown in FIG. 1 is capable of reducing, compared to conventional technology, the time from the start of lighting of the light source 5 to stabilization of the baseline, that is, the time from the start of lighting of the light source 5 to stabilization of the optical axis in the spectrometer 3.

Figure 4:
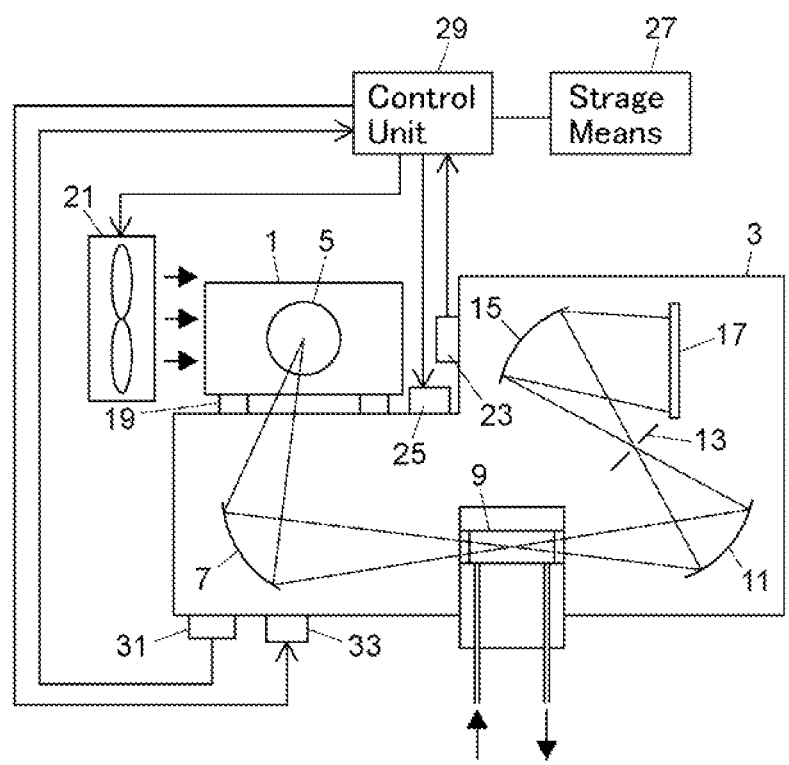
FIG. 4 is a diagram schematically showing a configuration of another embodiment.

FIG. 4 is a diagram schematically showing a configuration of another embodiment. Parts in FIG. 4 that serve the same functions as those in FIG. 1 are denoted with the same reference signs, and description thereof will be omitted.

Compared to the embodiment in FIG. 1, the present embodiment further includes a thermistor 31, and a heater 33. The set of thermistor 31 and heater 33 is for performing temperature measurement and heating of a spectrometer 3 at a position different from the set of the thermistor 23 and heater 25.

Storage means 27 stores, for each of the thermistors 23 and 31, the detection temperature of the thermistor 23 or 31 at the time the optical axis is stable in the spectrometer 3.

A control unit 29 causes the heaters 25 and 33 to operate when a light source 5 is illuminated from a light-off state. Also, the control unit 29 keeps a fan 21 in a stopped state.

The control unit 29 stops the heater 25 when the detection temperature of the thermistor 23 reaches the corresponding detection temperature stored in the storage means 27. Also, the control unit 29 stops the heater 33 when the detection temperature of the thermistor 31 reaches the corresponding detection temperature stored in the storage means 27. Furthermore, the control unit 29 causes the fan 21 to operate at a predetermined number of revolutions so that the temperature of a lamp house 1 is stabilized, when the detection temperature of one or both of the thermistors 23 and 31 reach the corresponding detection temperature stored in the storage means 27.

According to this operation, the temperature distribution of the spectrometer 3 at the time the optical axis is stable in the spectrometer 3 is achieved faster compared to a case where there is one set of thermistor and heater, and the time from the lighting of the light source 5 to the stabilization of the optical axis in the spectrometer 3 is further reduced.

Two sets of thermistors and heaters are provided in the embodiment in FIG. 4, but the spectroscopic device of the present invention may include three or more sets of thermistors and heaters.

Moreover, the arrangement of the thermistor 23 and the heater 25 shown in FIGS. 1 and 4, and the arrangement of the thermistor 31 and the heater 33 shown in FIG. 4 are only examples, and the arrangement positions of the sets of thermistors and heaters are arbitrary.

The embodiments described above are examples of the present invention, and various modifications are possible within the scope of the present invention.

In the embodiments described above, the operation of the fan 21 is controlled based on the detection temperature of the thermistor 23 or 31. However, the present invention is not limited to be such. For example, temperature measurement means for a lamp house for measuring the temperature of the lamp house 1 may be further provided, and the fan 21 may be made to operate at a predetermined number of revolutions when the temperature of the lamp house 1 reaches a predetermined temperature, as disclosed in Patent Document 1. The operation of the fan 21 is controlled by, for example, the control unit 29. This prevents the lamp house 1 to be heated more than necessary. Also, the time until the lamp house 1 is stabilized at a predetermined temperature is reduced.

Also, the storage means 27 may store, instead of the detection temperature of the thermistor 23 or 31, the time after the light source 5 is illuminated from the light-off state until the detection temperature of the thermistor 23 or 31 reaches the detection temperature at the time the optical axis is stable in the spectrometer 3 according to the operation of the heater 25 or 33. In this case, the control unit 29 causes the heater 25 or 33 to operate from the start of lighting of the light source 5 based on the time stored in the storage means 27. Also in this case, the spectrometer 3 is appropriately heated, as in the case where the heater 25 or 33 is operated based on the detection temperature of the thermistor 23 or 31, and the time from the start of lighting of the light source 5 to stabilization of the optical axis in the spectrometer 3 can be reduced.

Furthermore, the thermistors 23 and 31, and the heaters 25 and 33 are arranged on the outer surface of the housing of the spectrometer 3, but the arrangement positions of the thermistors 23 and 31, and the heaters 25 and 33 may be on the inside of the housing of the spectrometer 3.

Moreover, in the embodiments described above, the thermistors 23 and 31 are used as the temperature measurement means, and the heaters 25 and 33 are used as the heating means. However, the present invention is not limited to such. The temperature measurement means may be configured in any way as long as it is capable of measuring the temperature of the spectrometer 3 at a predetermined position. The heater may be configured in any way as long as it is capable of heating the spectrometer 3 at a predetermined position.

Moreover, the configuration of the lamp house 1 and the configuration of the spectrometer 3 described in the embodiments above are only examples. For example, the lamp house of the spectroscopic device of the present invention may include a focusing lens, as disclosed in Patent Document 1.

Further, according to the embodiments described above, the present invention is applied to a PDA absorbance detector for a liquid chromatograph, but the spectroscopic device to which the present invention is applied is not limited to such. The present invention is applicable to a spectroscopic device including a lamp house accommodating a light source inside, and a spectrometer for dispersing light from the lamp house. For example, the present invention may be applied to an absorption spectrophotometer, a spectrofluorometer, a UV detector for a liquid chromatograph, a fluorescence detector, and the like.

DESCRIPTION OF REFERENCE SIGNS

1: Lamp house
3: Spectrometer
5: Light source
21: Fan
23, 31: Thermistor (Temperature measurement means)
25, 33: Heater (Heating means)
27: Storage means
29: Control unit

The invention claimed is:

1. A spectroscopic device comprising:
   a lamp house accommodating a light source inside;
   a spectrometer positioned to receive light from the light source;
   temperature measurement means provided on the spectrometer, for measuring a temperature of the spectrometer;
   heating means provided on the spectrometer and configured separately from the lamp house, for heating the spectrometer;
   storage means for storing a detection temperature of the temperature measurement means at a time a base line of a chromatogram is stable in a state where the light source is illuminated; and
   a control unit configured to control an operation of the heating means, and to cause the heating means to operate, when the light source is illuminated from a light-off state, only until a detection temperature of the temperature measurement means reaches the detection temperature stored in the storage means.

2. The spectroscopic device according to claim 1, further comprising:
   a fan configured to cool the lamp house,
   wherein the control unit keeps the fan stopped when the light source is illuminated from the light-off state, and causes the fan to operate at a predetermined number of revolutions after the detection temperature of the temperature measurement means has reached the detection temperature stored in the storage means.

3. The spectroscopic device according to claim 2, comprising:
   a plurality of sets of the temperature measurement means and the heating means for performing temperature measurement and heating of the spectrometer at different positions, said plurality of sets of the temperature measurement means and the heating means being provided on the spectrometer,
   wherein the storage means stores, for each temperature measurement means, the detection temperature of the temperature measurement means at a time the optical axis is stable in the spectrometer, and
   wherein the control unit causes the plurality of heating means to operate based on the detection temperatures of the corresponding temperature measurement means.

4. The spectroscopic device according to claim 3,
   wherein the storage means stores, instead of the detection temperature, a time after the light source is illuminated from the light-off state until the detection temperature of the temperature measurement means reaches the detection temperature at a time the optical axis is stable in the spectrometer according to an operation of the heating means, and
   wherein the control unit causes the heating means to operate, based on the time stored in the storage means.

5. The spectroscopic device according to claim 2,
   wherein the storage means stores, instead of the detection temperature, a time after the light source is illuminated from the light-off state until the detection temperature of the temperature measurement means reaches the detection temperature at a time the optical axis is stable in the spectrometer according to an operation of the heating means, and
   wherein the control unit causes the heating means to operate, based on the time stored in the storage means.

6. The spectroscopic device according to claim 1, comprising:
   a plurality of sets of the temperature measurement means and the heating means for performing temperature measurement and heating of the spectrometer at different positions, said plurality of sets of the temperature measurement means and the heating means being provided on the spectrometer,
   wherein the storage means stores, for each temperature measurement means, the detection temperature of the temperature measurement means at a time the optical axis is stable in the spectrometer, and
   wherein the control unit causes the plurality of heating means to operate based on the detection temperatures of the corresponding temperature measurement means.

7. The spectroscopic device according to claim 6,
   wherein the storage means stores, instead of the detection temperature, a time after the light source is illuminated from the light-off state until the detection temperature of the temperature measurement means reaches the detection temperature at a time the optical axis is stable in the spectrometer according to an operation of the heating means, and
   wherein the control unit causes the heating means to operate, based on the time stored in the storage means.

8. The spectroscopic device according to claim 1,
   wherein the storage means stores, instead of the detection temperature, a time after the light source is illuminated from the light-off state until the detection temperature of the temperature measurement means reaches the detection temperature at a time the optical axis is stable in the spectrometer according to an operation of the heating means, and
   wherein the control unit causes the heating means to operate, based on the time stored in the storage means.

* * * * *